US010159595B2

(12) United States Patent
Chen et al.

(10) Patent No.: US 10,159,595 B2
(45) Date of Patent: Dec. 25, 2018

(54) NEGATIVE PRESSURE GENERATING DEVICE AND APPLICATION THEREOF

(71) Applicant: SOMNICS, INC., Zhubei, Hsinchu County (TW)

(72) Inventors: Yin-Ruei Chen, Zhubei (TW); Tung-Ming Yu, Zhubei (TW); Chen-Ning Huang, Zhubei (TW); Chung-Chu Chen, Zhubei (TW)

(73) Assignee: SOMNICS, INC., Zhubei, Hsinchu County (TW)

( * ) Notice: Subject to any disclaimer, the term of this patent is extended or adjusted under 35 U.S.C. 154(b) by 122 days.

(21) Appl. No.: 15/308,048

(22) PCT Filed: Dec. 5, 2014

(86) PCT No.: PCT/CN2014/093160
§ 371 (c)(1),
(2) Date: Oct. 31, 2016

(87) PCT Pub. No.: WO2016/086418
PCT Pub. Date: Jun. 9, 2016

(65) Prior Publication Data
US 2017/0049606 A1 Feb. 23, 2017

(51) Int. Cl.
A61F 5/56 (2006.01)
A61M 16/00 (2006.01)
A61M 16/04 (2006.01)

(52) U.S. Cl.
CPC .............. A61F 5/566 (2013.01); A61F 5/56 (2013.01); A61M 16/0009 (2014.02);
(Continued)

(58) Field of Classification Search
CPC ........... A61F 5/56; A61F 5/566; A61M 16/00; A61M 16/0003; A61M 16/0009;
(Continued)

(56) References Cited

U.S. PATENT DOCUMENTS 5,957,133 A 9/1999 Hart
7,398,855 B2 7/2008 Seel
(Continued)

FOREIGN PATENT DOCUMENTS

CN 1715674 A 1/2006
CN 1901960 A 1/2007
(Continued)

OTHER PUBLICATIONS

European Communication pursuant to Article 94(3) EPC for Application No. 14907504.6, dated Sep. 4, 2017.
(Continued)

Primary Examiner — Tan-Uyen T Ho
Assistant Examiner — Joseph D Boecker
(74) Attorney, Agent, or Firm — Birch, Stewart, Kolasch & Birch, LLP

(57) ABSTRACT

The present invention provides a negative pressure generator comprising a vacuum pump having an intake end and an exhaust end, a soundproofing module having a compartment for accommodating the vacuum pump, the soundproofing module being configured to insulate noise and vibration generated when the vacuum pump is in operation, and a silencing tube module comprising a flexible intake tube having one open end communicating with the intake end of the vacuum pump and a flexible exhaust tube having one open end communicating with the exhaust end of the vacuum pump, the silencing tube module being configured to reduce noise generated at the intake end and/or the exhaust end of the vacuum pump when the vacuum pump is in operation. The negative pressure generator can provide a vacuum source to an oral interface device to favorably create a negative pressure environment in a user's oral cavity so that the patency of the user's upper airway is maintained.

10 Claims, 13 Drawing Sheets

(52) U.S. Cl.
CPC ...... *A61M 16/0057* (2013.01); *A61M 16/049* (2014.02); *A61M 2016/0027* (2013.01); *A61M 2205/18* (2013.01); *A61M 2205/3331* (2013.01); *A61M 2205/42* (2013.01); *A61M 2205/8206* (2013.01); *A61M 2205/8262* (2013.01)

(58) Field of Classification Search
CPC ............ A61M 16/0057; A61M 16/049; A61M 1/0066; A61M 1/06; A61M 1/10; A61M 1/101; F04D 17/168; F04D 19/04; F04D 19/042; F04D 29/663; F04D 29/664
USPC .................................................... 128/205.19
See application file for complete search history.

(56) References Cited

U.S. PATENT DOCUMENTS

| | | | |
|---|---|---|---|
| 7,918,222 | B2 | 4/2011 | Chen |
| 2005/0103339 | A1 | 5/2005 | Daly et al. |
| 2007/0068526 | A1* | 3/2007 | Lang ................. A61M 16/0057 128/204.22 |
| 2008/0304986 | A1* | 12/2008 | Kenyon ............ A61M 16/0066 417/423.12 |
| 2010/0116583 | A1* | 5/2010 | Seedorf ................ F04B 53/002 181/205 |
| 2010/0185165 | A1* | 7/2010 | Middleton .......... A61M 1/0031 604/319 |
| 2011/0017544 | A1* | 1/2011 | Bodwell ................ F04B 35/06 181/200 |
| 2012/0053542 | A1* | 3/2012 | Wu ..................... A61M 1/0066 604/319 |
| 2012/0301267 | A1* | 11/2012 | Baecke ............. A61M 16/0057 415/1 |
| 2014/0034064 | A1 | 2/2014 | Chen et al. |
| 2014/0299406 | A1* | 10/2014 | Librett .................. A61M 16/08 181/224 |
| 2014/0343518 | A1 | 11/2014 | Riesinger |

FOREIGN PATENT DOCUMENTS

| | | | | |
|---|---|---|---|---|
| CN | 101143115 | A | 3/2008 | |
| CN | 201200652 | Y | 3/2009 | |
| CN | 101917924 | A | 12/2010 | |
| CN | 203189231 | U | 9/2013 | |
| CN | 103976814 | A | 8/2014 | |
| CN | 104023762 | A | 9/2014 | |
| DE | 102004002031 | A1 * | 8/2005 | ........ A61M 16/0057 |
| EP | 2 301 490 | B1 | 6/2016 | |
| GB | 2485417 | A | 5/2012 | |
| JP | 2007-510481 | A | 4/2007 | |
| JP | 2007-319680 | A | 12/2007 | |
| JP | 2011-502715 | A | 1/2011 | |
| WO | WO 99/22793 | A1 | 5/1999 | |
| WO | WO 2008/028247 | A1 | 3/2008 | |
| WO | WO 2009/064914 | A1 | 5/2009 | |

OTHER PUBLICATIONS

Extended European Search Report for Application No. 14907504.6, dated Dec. 20, 2016.

Japanese Notice of Allowance and English translation for Application No. 2017-529724, dated May 8, 2018.

* cited by examiner

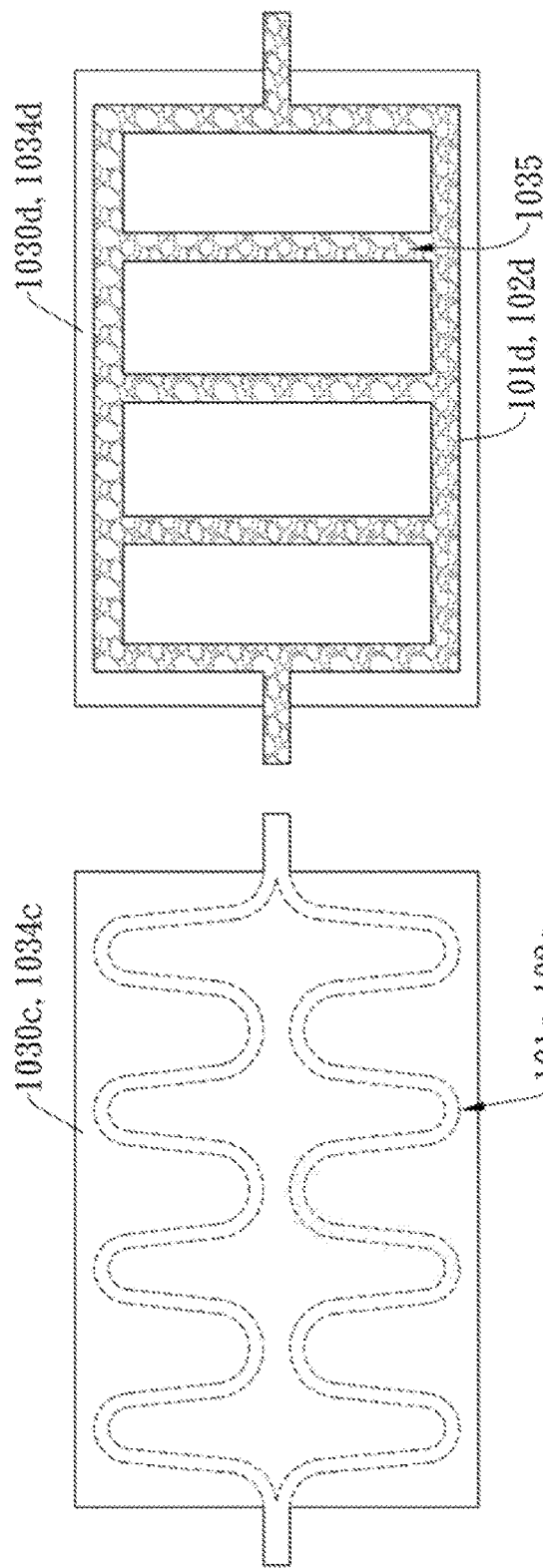

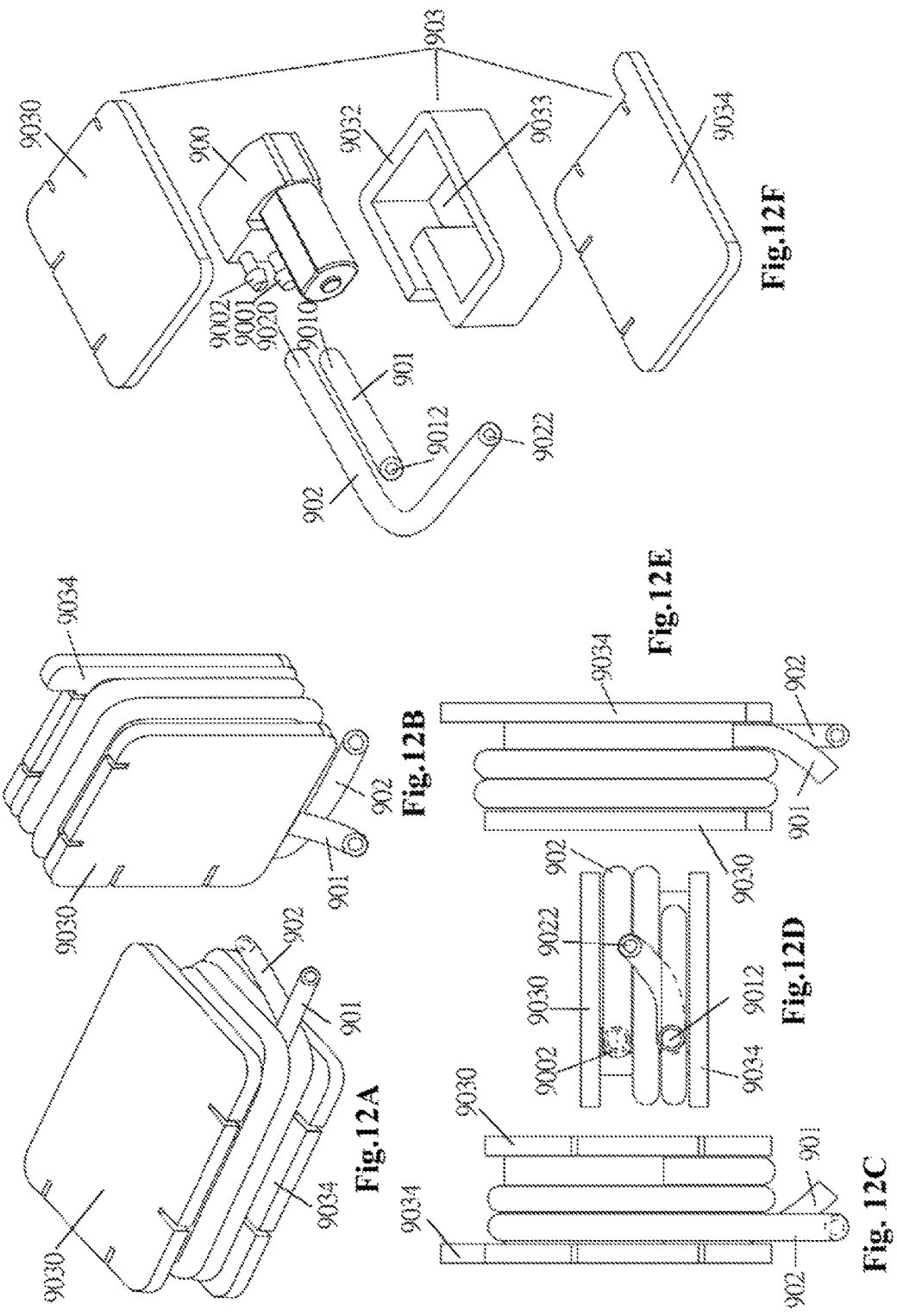

NEGATIVE PRESSURE GENERATING DEVICE AND APPLICATION THEREOF

BACKGROUND OF THE INVENTION

Field of the Invention

The present invention relates to a negative pressure generator, and more particularly, to a negative pressure generator for providing a vacuum source to an oral interface device placed in an oral cavity of a patient with sleep breathing problem.

Prior Art

Obstructive sleep apnea (OSA), hypopnea, and upper airway resistance syndrome (UARS) are among a variety of known disorders characterized by episodes of complete or partial upper airway blockage during sleep, anesthetization, or post anesthesia. OSA, hypopnea, and UARS cause intermittent interruption of breathing during sleep with the consequence of potentially severe oxyhemoglobin desaturation. Typically, those afflicted with OSA, hypopnea, and/or UARS experience repeated, frequent arousal from sleep in response to the oxygen deprivation. The arousals result in sleep fragmentation and poor sleep continuity.

The use of a Constant Positive Airway Pressure (CPAP) machine is the most common treatment for OSA patients among the current treatment option. The CPAP machine which consists of a mask, a pump and a humidifier continuously blows pressurized air into a patient's nose to keep his/her airway open during sleep. The CPAP machine is quite effective; however, it causes unpleasant side effects such as dry throat and nasal congestion. Patients who use the CPAP machine often have swollen nasal mucosa and experience headaches in the morning. The treatment with the CPAP machine has a low patient compliance because of its significant side effects.

Currently, an improved treatment of OSA involves applying a negative pressure to a forward end of a patient's oral cavity, typically at or just behind the lips so that the negative pressure will pull his/her tongue forward to lift the rear portion of the tongue away from the back of the airway. Various oral devices using oral negative pressure, such as the oral interface device disclosed in the PCT International Patent Application No. PCT/US14/11129 filed on Jan. 10, 2014, have been developed to facilitate breathing for those suffering from OSA, hypopnea, and/or UARS by properly controlling negative pressure applied to the oral cavity. Moreover, oral devices using oral negative pressure can use a negative pressure control system, such as an electronic pump disclosed in the U.S. Patent Publication No. 2009/0288660 or the like, to provide a vacuum source.

SUMMARY OF THE INVENTION

An object of the present invention is to provide a negative pressure generator for providing a vacuum source to oral interface devices for treating patients with sleep breathing problem.

Another object of the present invention is to provide a portable negative pressure generator for the user's convenience.

Another object of the present invention is to provide a negative pressure generator with reduced noise interference so that the user can have a quiet and comfortable sleeping environment.

Another object of the present invention is to utilize a soundproofing module enclosing a vacuum pump of a negative pressure generator and a silencing tube structure as a combination of an intake tube and an exhaust tube for the vacuum pump so as to reduce noise and vibration generated when the vacuum pump is in operation.

Another object of the present invention is to utilize a single tube in a loop configuration, a plurality of tubes connected in parallel or a multiply bent tube as an intake tube and/or an exhaust tube for a vacuum pump so that the length of the intake/exhaust tube can be extended without increasing the size of the negative pressure generator of the present invention, thereby reducing noise generated at the intake end and/or the exhaust end when the vacuum pump is in operation.

In one aspect, the present invention provides a negative pressure generator, comprising: a vacuum pump having an intake end and an exhaust end; a soundproofing module having a compartment for accommodating the vacuum pump, the soundproofing module being configured to insulate noise and vibration generated when the vacuum pump is in operation; and a silencing tube module comprising a flexible intake tube having one open end communicating with the intake end of the vacuum pump and a flexible exhaust tube having one open end communicating with the exhaust end of the vacuum pump, the silencing tube module being configured to reduce noise generated at the intake end and/or the exhaust end of the vacuum pump when the vacuum pump is in operation and disposed on a surface of the soundproofing module or embedded into a main body of the soundproofing module.

In some embodiments of the present invention, the soundproofing module and/or the silencing tube module can be made of a material selected from the group consisting of silicone, plastic, ethylene vinyl acetate copolymer (EVA) and polyurethane (PU).

In some embodiments of the present invention, the flexible intake tube and/or the flexible exhaust tube of the silencing tube module can be in a form of a single tube in a loop configuration, a plurality of tubes connected in parallel or a multiply bent tube so that the length(s) of the flexible intake tube and/or the flexible exhaust tube of the silencing tube module can be extended without increasing the size of the negative pressure generator, thereby reducing noise generated at the intake end and/or the exhaust end when the vacuum pump of the negative pressure generator is in operation. For example, in one embodiment of the present invention, the flexible exhaust tube is a single tube winding around the exterior of the soundproofing module in a multiple loop configuration. In one embodiment of the present invention, the flexible exhaust tube comprises a plurality of individual tubes connected in parallel and winding around the exterior of the soundproofing module. In one embodiment of the present invention, the soundproofing module comprises a first cover member, an intermediate housing and a second cover member, and the flexible exhaust tube comprises at least one first multiply bent tube disposed inside the first cover member. In one embodiment of the present invention, the flexible exhaust tube comprises a plurality of first multiply bent tubes connected in parallel and disposed inside the first cover member. In one embodiment of the present invention, the flexible exhaust tube is arranged in a grating-shaped loop configuration on a surface of the first cover member opposite to the surface thereof facing the vacuum pump, and a porous material is filled in the flexible exhaust tube. In one embodiment of the present invention, the flexible intake tube comprises at least one second multiply bent tube disposed inside the second cover member. In one embodiment of the present invention, the flexible intake tube comprises a plurality of second multiply bent tubes connected in parallel and disposed inside the second cover member. In one embodiment of the present invention, the flexible intake tube is arranged in a grating-shaped loop configuration on a surface of the second cover member opposite to the surface thereof facing the vacuum pump, and a porous material is filled in the flexible intake tube.

In one embodiment of the present invention, the negative pressure generator is a portable device with a built-in power supply.

In another aspect, the present invention provides an apparatus for generating negative pressure in the oral cavity, comprising a negative pressure generator of the present invention and an oral interface device. The oral interface device comprises an oral interface and an air conduit having an inlet and an outlet and passing through the oral interface. The oral interface is placed in a user's oral cavity to secure the inlet of the air conduit therein, and the outlet of the air conduit communicates with the other open end of the flexible intake tube. The air conduit, the flexible intake tube, the vacuum pump and the flexible exhaust tube constitute a negative pressure path so as to create a negative pressure environment in the user's oral cavity.

For the soundproofing module and the silencing tube module of the negative pressure generator of the present invention, the above applicable materials and the various embodiments thereof can be used in the apparatus for generating negative pressure in the oral cavity of the present invention.

BRIEF DESCRIPTION OF THE DRAWINGS

FIG. 7 is a schematic view showing a third variation of the vacuum pump module of the negative pressure generator according to the first embodiment of the present invention.

FIG. 8 is a schematic view showing a fourth variation of the vacuum pump module of the negative pressure generator according to the first embodiment of the present invention.

FIG. 12A is a perspective view showing the appearance of a vacuum pump module of the negative pressure generator according to the second embodiment of the present invention.

FIG. 12B is a perspective view showing the appearance of the vacuum pump module of FIG. 12A rotated counterclockwise for 90 degrees.

FIG. 12C is a schematic view showing one long lateral side of the vacuum pump module of the negative pressure generator according to the second embodiment of the present invention.

FIG. 12D is a schematic view showing one short lateral side of the vacuum pump module of the negative pressure generator according to the second embodiment of the present invention.

FIG. 12E is a schematic view showing the other long lateral side of the vacuum pump module of the negative pressure generator according to the second embodiment of the present invention.

FIG. 12F is a perspective exploded view of the vacuum pump module of the negative pressure generator according to the second embodiment of the present invention.

DETAILED DESCRIPTION OF PREFERRED EMBODIMENTS OF THE INVENTION

Figure 1B:
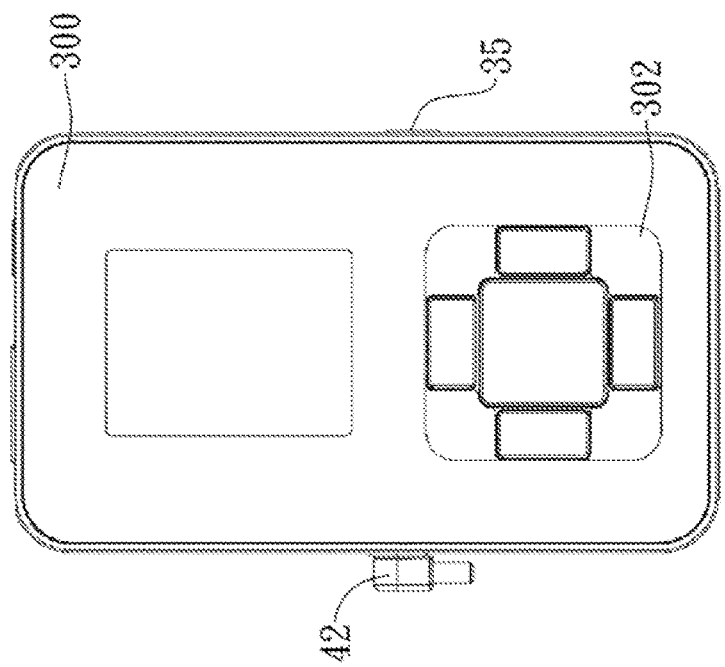
FIG. 1B shows a bottom view of the negative pressure generator according to the first embodiment of the present invention.

The objects, spirits and advantages of the present invention will be apparent from the following description of preferred embodiments thereof and the accompanying drawings. It should be noted that in order to clearly show the structures and arrangement relationship of certain important components of the present invention, the components in the drawings may not be illustrated according to actual scale, and certain components may be illustrated with some parts thereof omitted in some drawings and the main structures thereof disclosed in other drawings.

Figure 1A:
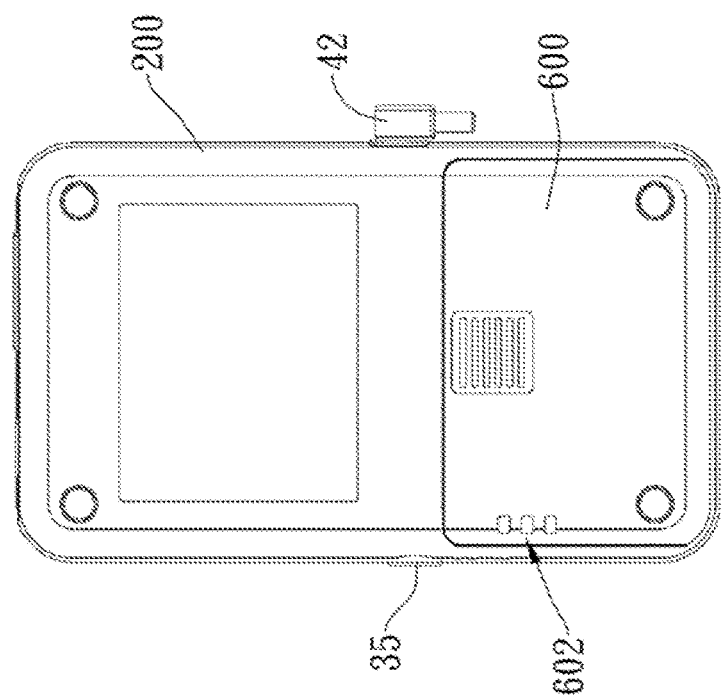
FIG. 1A shows a top view of a negative pressure generator according to a first embodiment of the present invention.
Figure 1C:
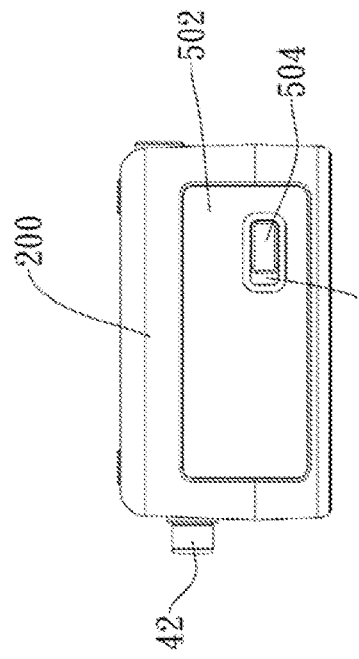
FIG. 1C shows a front view of the negative pressure generator relative to the bottom view of FIG. 1B according to the first embodiment of the present invention.
Figure 1D:
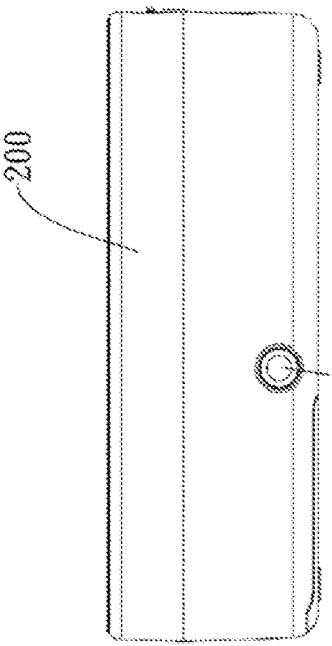
FIG. 1D shows a rear view of the negative pressure generator relative to the bottom view of FIG. 1B according to the first embodiment of the present invention.
Figure 1E:
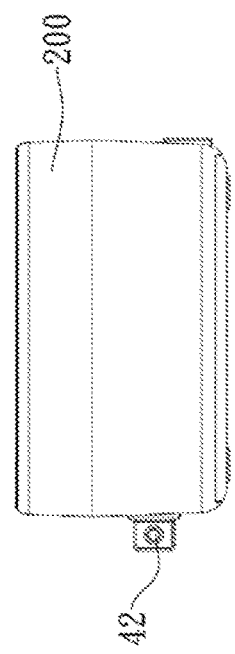
FIG. 1E shows a left side view of the negative pressure generator relative to the bottom view of FIG. 1B according to the first embodiment of the present invention.
Figure 1F:
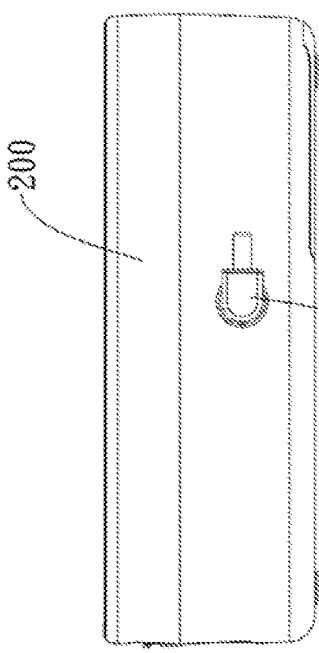
FIG. 1F shows a right side view of the negative pressure generator relative to the bottom view of FIG. 1B according to the first embodiment of the present invention.
Figure 2:
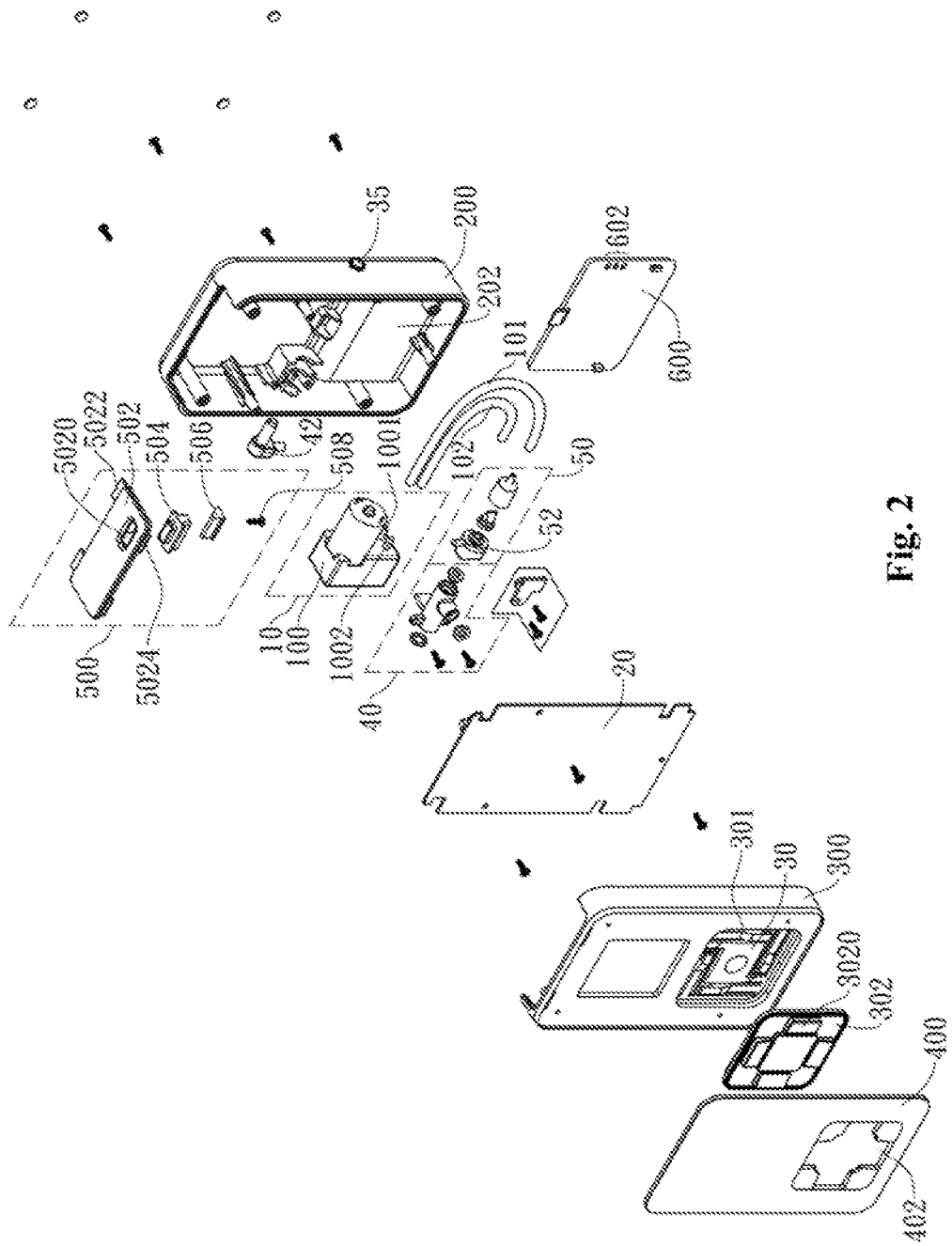
FIG. 2 shows a perspective exploded view of the negative pressure generator according to the first embodiment of the present invention.
Figure 3:
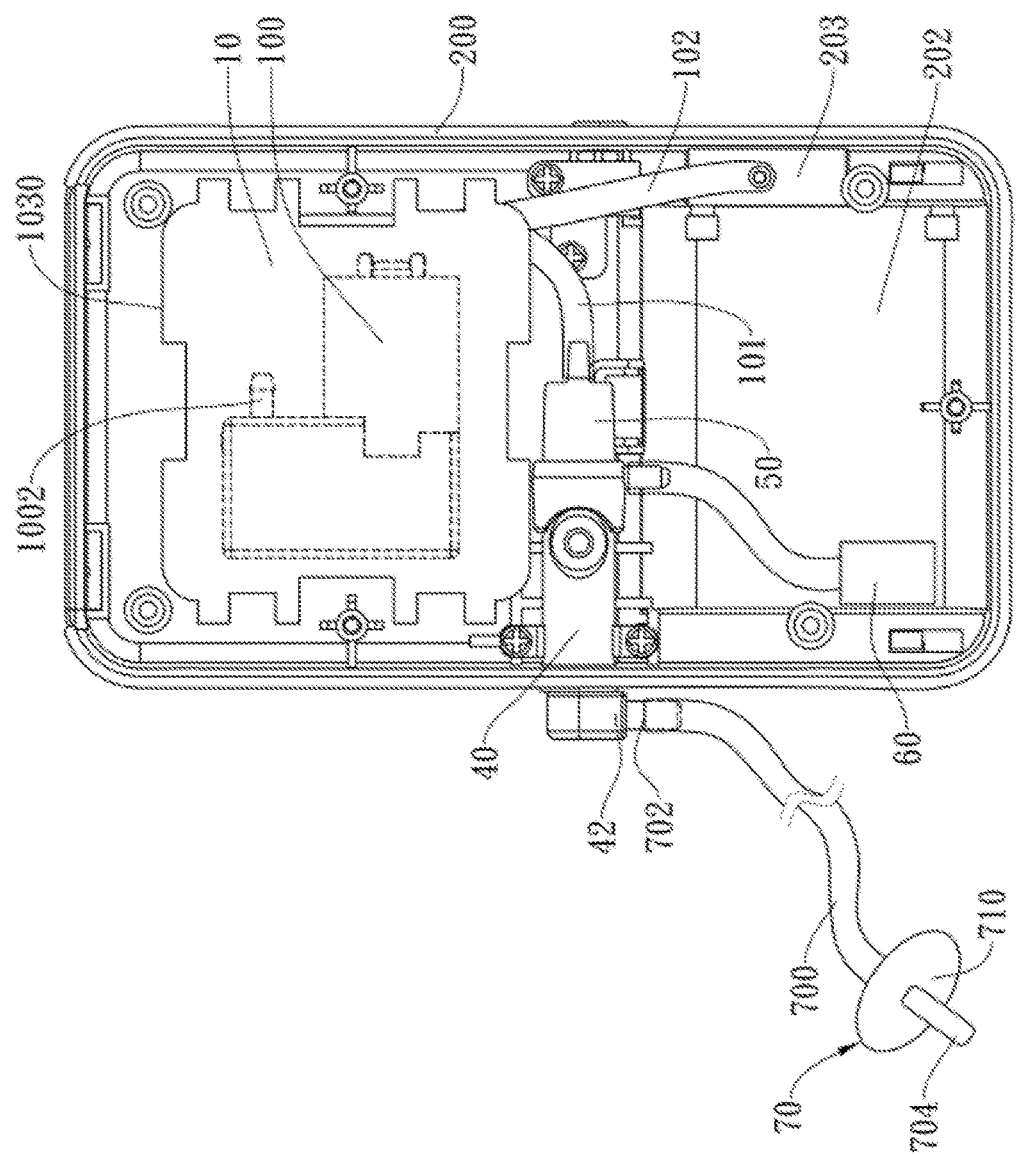
FIG. 3 is a diagram showing an arrangement relation among the components of a bottom housing module of the negative pressure generator connected with an oral interface device according to the first embodiment of the present invention.

FIGS. 1A to 1F, FIG. 2 and FIG. 3 show a negative pressure generator according to the first embodiment of the present invention. FIG. 1A through FIG. 1F illustrates various aspects of the appearance of the negative pressure generator according to the first embodiment of the present invention, in which FIG. 1A is a top view, FIG. 1B is a bottom view, FIG. 1C is a front view relative to the bottom view of FIG. 1B, FIG. 1D is a rear view relative to the bottom view of FIG. 1B, FIG. 1E is a left side view relative to the bottom view of FIG. 1B, and FIG. 1F is a right side view relative to the bottom view of FIG. 1B. FIG. 2 is a perspective exploded view of the negative pressure generator according to the first embodiment of the present invention. FIG. 3 is a diagram showing an arrangement relationship among the components of a bottom housing module of the negative pressure generator connected with an oral interface device according to the first embodiment of the present invention. The negative pressure generator is capable of providing a vacuum source to various oral interface devices for treating OSA. As shown in FIG. 2, the negative pressure generator mainly comprises a vacuum pump module 10, a control module 20, a bottom housing module 200, a top housing module 300, a front cover module 500 and a power supply source. In the first embodiment, the power supply source can supply power by connecting to an external power source via an external power source connection port 35. Alternatively, the power supply source is a battery pack (not shown) installed in the battery holder 202 formed in a lower compartment of the bottom housing module 200. Referring to FIG. 1A, a battery protective cover 600 is arranged at the lower portion of the back of the bottom housing module 200 to cover the battery holder 202. The battery protective cover 600 defines a plurality of exhaust vents 602 at one side thereof close to the external power source connection port 35.

Figure 4:
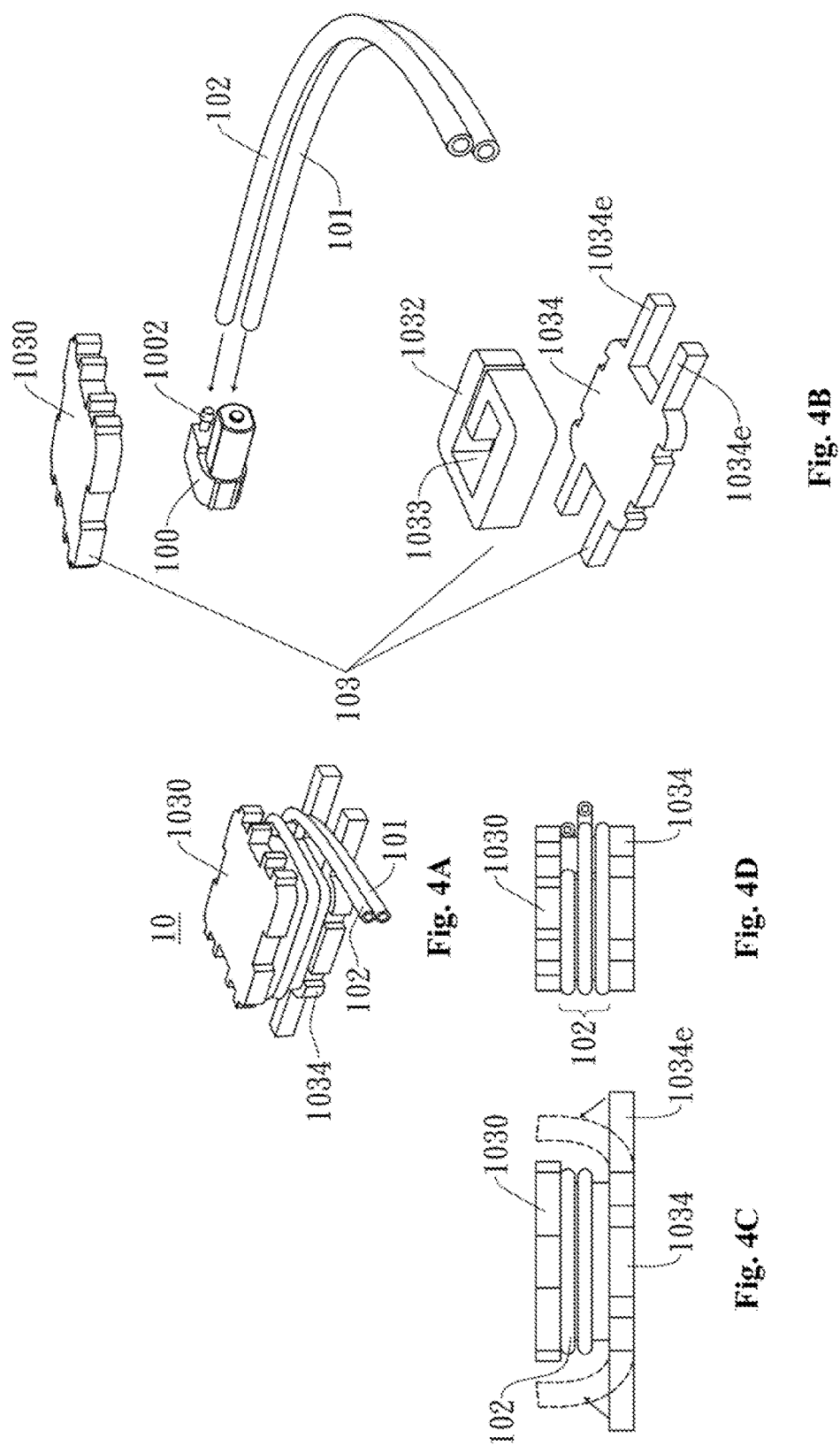
FIG. 4A is a perspective view showing the appearance of a vacuum pump module of the negative pressure generator according to the first embodiment of the present invention.
FIG. 4B is a perspective exploded view of the vacuum pump module of the negative pressure generator according to the first embodiment of the present invention.
FIG. 4C is a schematic view showing one side of the vacuum pump module of the negative pressure generator according to the first embodiment of the present invention.
FIG. 4D is a schematic view showing another side of the vacuum pump module of the negative pressure generator according to the first embodiment of the present invention.

Referring to FIG. 4A through FIG. 4D and FIG. 2, the vacuum pump module 10 comprises a vacuum pump 100, a flexible intake tube 101, a flexible exhaust tube 102 and a soundproofing module 103. The vacuum pump 100 has an intake end 1001 communicating with one open end of the flexible intake tube 101 and an exhaust end 1002 communicating with one open end of the flexible exhaust tube 102. The soundproofing module 103 encloses the vacuum pump 100; the flexible intake tube 101 extends from the intake end 1001 to the exterior of the soundproofing module 103; the flexible exhaust tube 102 extends from the exhaust end 1002 and winds around the exterior of the soundproofing module 103 in a multiple loop configuration; one open end of the flexible exhaust tube 102 opposite to the open end thereof facing the exhaust end 1002 passes through a hole 203 (see FIG. 3) defined at the side of the bottom housing module 200 close to the external power source connection port 35 to communicate with the exhaust vent 602 defined on the battery protective cover 600 to discharge, via the exhaust vent 602, air sucked by the vacuum pump 100 to the ambient environment. The soundproofing module 103 can insulate the ambient environment against noise and vibration generated when the vacuum pump 100 is in operation. In one embodiment of the present invention, the soundproofing module 103 can be made of a porous sound absorbing material, such as a sound absorbing foam, e.g., polyurethane (PU) foam, polyethylene (PE) foam, etc. In some embodiments of the present invention, the soundproofing module 103 can be made of a material selected from a group consisting of silicone, plastic (e.g., PMMA, PC, PP), EVA and PU. In one embodiment of the present invention, the soundproofing module 103 can comprise a first cover member 1030, an intermediate housing 1032 having a hollow chamber 1033 for accommodating the vacuum pump 100 (see FIG. 4B), and a second cover member 1034. As shown in FIG. 4A, FIG. 4C and FIG. 4D, the flexible exhaust tube 102 winds around the exterior of the soundproofing module 103 in a multiple loop configuration. With such a multiple loop configuration, the length of the flexible exhaust tube 102 can be extended without increasing the size of the vacuum pump module 10, thereby reducing noise generated at the exhaust end 1002 of the vacuum pump 100 when the vacuum pump 100 is in operation. In some embodiments of the present invention, the flexible intake tube 101 and the flexible exhaust tube 102 can be made of a material selected from a group consisting of silicone, plastic (e.g., PMMA, PC, PP), EVA and PU.

Figure 5:
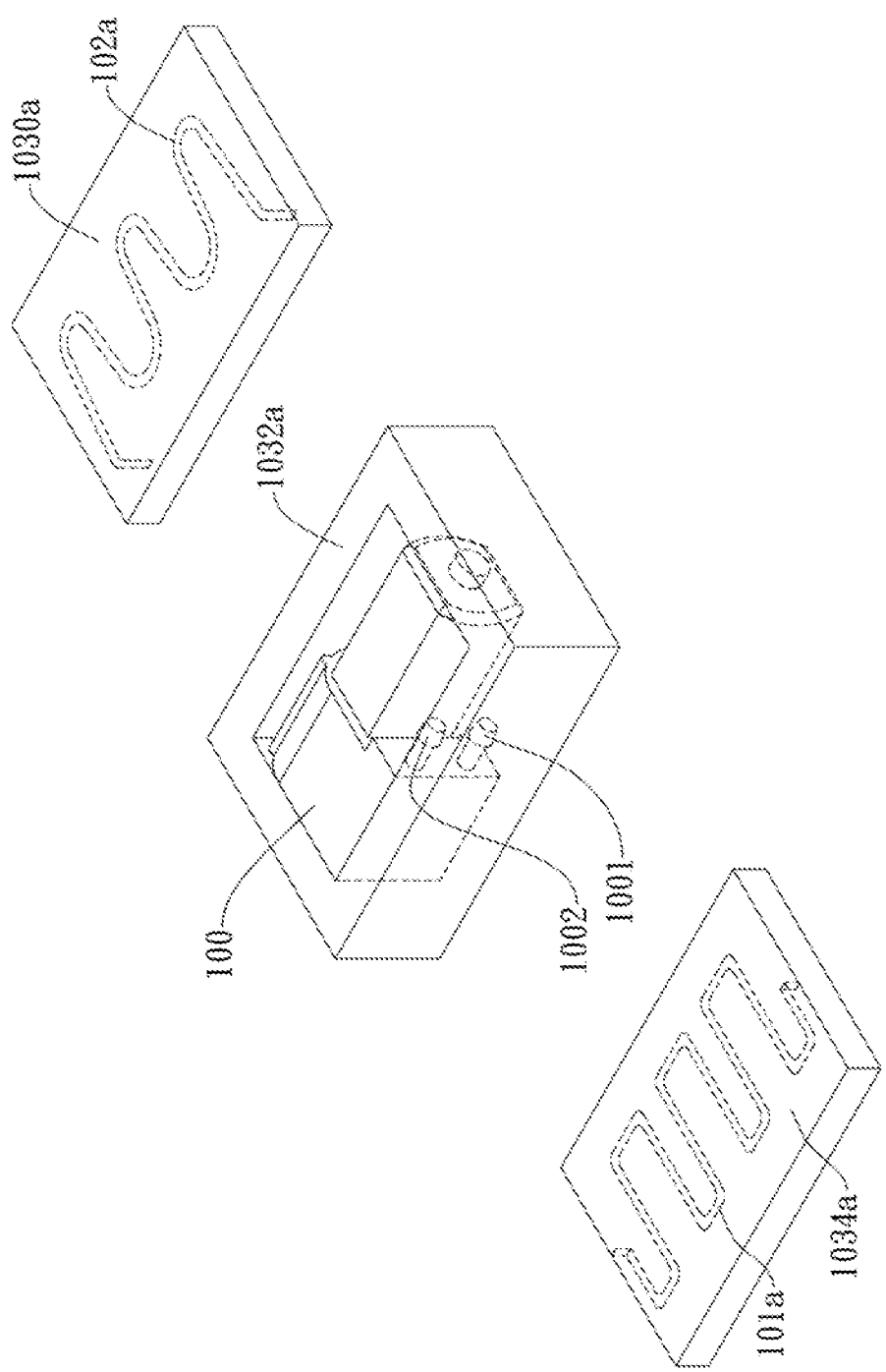
FIG. 5 is a schematic view showing a first variation of the vacuum pump module of the negative pressure generator according to the first embodiment of the present invention.
Figure 6:
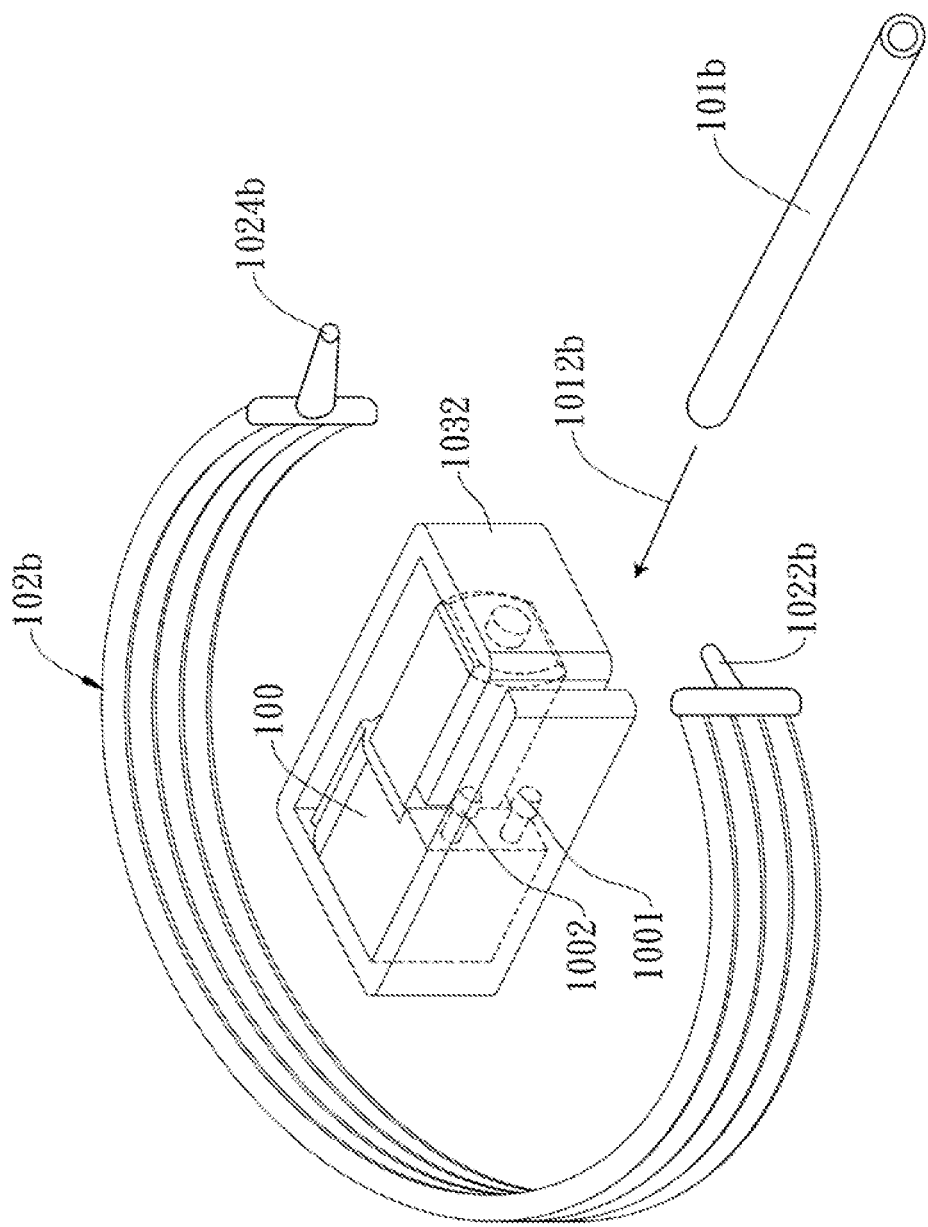
FIG. 6 is a schematic view showing a second variation of the vacuum pump module of the negative pressure generator according to the first embodiment of the present invention.

The flexible intake tube 101 and/or the flexible exhaust tube 102 of the present invention can adopt other configurations to extend the length(s) thereof without increasing the size of the vacuum pump module 10, thereby reducing noise generated at the intake end 1001 and/or the exhaust end 1002 when the vacuum pump 100 is in operation. For example, FIG. 5 shows a first variation of the vacuum pump module of the present invention. In the first variation, the vacuum pump module comprises a vacuum pump 100 having an intake end 1001 and an exhaust end 1002, a soundproofing module (1030a, 1032a, 1034a), a flexible multiply bent intake tube 101a and a flexible multiply bent exhaust tube 102a. The soundproofing module comprises a first cover member 1030a, an intermediate housing 1032a having a hollow chamber for accommodating the vacuum pump 100, and a second cover member 1034a. The flexible intake tube 101a is disposed inside the second cover member 1034a with one open end thereof extending out of the second cover member 1034a to communicate with the intake end 1001 of the vacuum pump 100 and the other open end thereof extending out of the second cover member 1034a. The flexible exhaust tube 102a is disposed inside the first cover member 1030a with one open end thereof extending out of the first cover member 1030a to communicate with the exhaust end 1002 of the vacuum pump 100 and the other open end thereof extending out of the first cover member 1030a. In one embodiment of the present invention, the flexible intake tube 101a and the second cover member 1034a can be formed integrally through injection molding. The flexible exhaust tube 102a and the first cover member 1030a can be formed integrally through injection molding. FIG. 6 shows a second variation of the vacuum pump module of the present invention. In the second variation, the vacuum pump module is different from the vacuum pump module 10 of the first embodiment in that the flexible exhaust tube 102b comprises a plurality of flexible tubes connected in parallel and clustered at the open ends 1022b and 1024b. The open end 1022b communicates with the exhaust end 1002 of the vacuum pump 100. The open end 1024b communicates with the ambient environment. The vacuum pump 100 is disposed in the hollow chamber 1033 of the intermediate housing 1032, and the flexible exhaust tube 102b comprising a plurality of flexible tubes connected in parallel winds around an exterior of the intermediate housing 1032. The intake end 1001 of the vacuum pump 100 communicates with a flexible intake tube 101b. It should be noted that in order to clearly show the structures and arrangement relationship of the components in FIG. 6, these components are not illustrated according to actual scale. FIG. 7 shows another variation of the flexible intake tube 101 and the flexible exhaust tube 102 of the present invention. In this variation of the present invention, a plurality of multiply bent tubes connected in parallel serve as the flexible intake tube 101c and the flexible exhaust tube 102c, which are disposed inside the second cover member 1034c and the first cover member 1030c of the soundproofing module, respectively. In one embodiment of the present invention, the flexible intake tube 101c and the second cover member 1034c can be integrally formed through injection molding, and the flexible exhaust tube 102c and the first cover member 1030c can be formed integrally through injection molding. In this variation of the present invention, the rest of the components of the vacuum pump module are the same as the corresponding components of the variation shown in FIG. 5, thus the descriptions thereof are not presented. Moreover, an ordinarily skilled person in the art can easily infer the complete structure of the vacuum pump module adopting the configuration of the flexible intake tube and the flexible exhaust tube illustrated in FIG. 7 from the vacuum pump module shown in FIG. 5. FIG. 8 shows another variation of the flexible intake tube 101 and the flexible exhaust tube 102 of the present invention. In this variation of the present invention, the flexible intake tube 101d and the flexible exhaust tube 102d are arranged in a grating-shaped loop configuration, and a porous material 1035 is filled in the flexible intake tube 101d and the flexible exhaust tube 102d. The flexible intake tube 101d is disposed on a surface of the second cover member 1034d of the soundproofing module opposite to the surface thereof facing the vacuum pump 100, and the flexible exhaust tube 102d is disposed on a surface of the first cover member 1030d of the soundproofing module opposite to the surface thereof facing the vacuum pump 100. In this variation of the present invention, the rest of the components of the vacuum pump module are the same as the corresponding components of the variation shown in FIG. 5, thus the descriptions thereof are not presented. Moreover, an ordinarily skilled person in the art can easily infer the complete structure of the vacuum pump module adopting the configuration of the flexible intake tube and the flexible exhaust tube illustrated in FIG. 8 from the vacuum pump module shown in FIG. 5.

Referring to FIG. 2 and FIG. 3, the negative pressure generator of the present invention further comprises a tri-way connector module 40 and a check valve module 50. For the tri-way connector module 40, one port thereof is connected to the check valve module 50, another port thereof communicates with a pressure relief valve 60, and another port thereof can communicate with an oral interface device 70 for generating negative pressure in the oral cavity. The oral interface device 70 has an air conduit 700 whose one open end 702 communicates with a corresponding port of the tri-way connector module 40 and whose the other open end 704 is placed in a user's oral cavity. The oral interface device 70 further comprises an oral interface 710 placed in the user's oral cavity to secure the open end 704 of the air conduit 700 in the oral cavity. The present invention can use the oral interface device disclosed in the PCT International Patent Application No. PCT/US14/11129 filed on Jan. 10, 2014 and incorporated herein by reference. The other open end of the check valve module 50 communicates with one open end of the flexible intake tube 101 opposite to the open end thereof facing the intake end 1001 of the vacuum pump. In one embodiment of the present invention, the air conduit 700 can communicate with the tri-way connector module 40 via an adaptor 42. When the negative pressure generator of the present invention provides a vacuum source to the oral interface device 70, the air conduit 700, the flexible intake tube 101, the vacuum pump 100 and the flexible exhaust tube 102 constitute a negative pressure path so as to favorably create a negative pressure environment in the user's oral cavity. The check valve module 50 can direct the flow of air in the negative pressure path from the air conduit 700 to the flexible exhaust tube 102. In one embodiment of the present invention, one open end of the flexible exhaust tube 102 opposite to the open end thereof facing the exhaust end 1002 of the vacuum pump can communicate with a saliva container (not shown). In one embodiment of the present invention, the negative pressure generator can include a pressure sensor (not shown) communicating with an air flow channel 52 of the check valve module 50 so as to measure a pressure value of the negative pressure path. The pressure sensor (not shown) can be disposed in the control module 20. When the pressure value of the negative pressure path reaches a threshold of the pressure relief valve 60, the pressure relief valve 60 will open to let the ambient air enter the negative pressure path to reduce the negative pressure in the user's oral cavity. Accordingly, the present invention can prevent discomfort to the user caused by excessively high negative pressure.

In one embodiment of the present invention, the power supply source of the negative pressure generator can be a battery pack installed in the battery holder 202 so that the negative pressure generator can be favorably manufactured as a portable device for the better convenience of users. The power supply source can be an external power source. For example, the negative pressure generator is connected to an external power source through the external power source connection port 35. The power supply source is electrically connected to the control module 20 through which the magnitude of the power supplied to the vacuum pump 100 can be controlled, thereby reaching the desired negative pressure value in the user's oral cavity. In one embodiment of the present invention, the control module 20 can adjust the magnitude of the power supplied to the vacuum pump 100 according to the negative pressure value detected by the pressure sensor. As shown in FIG. 3, the vacuum pump module 10, the tri-way connector module 40 and the check valve module 50 are mounted in the upper compartment of the bottom housing module 200; the battery holder 202 and the pressure relief valve 60 are mounted in the lower compartment of the bottom housing module 200. Referring to FIG. 4A and FIG. 4C, in one embodiment of the present invention, a pair of extension portions 1034e is respectively disposed at two opposing sides of the second cover member 1034 of the soundproofing module 103 of the vacuum pump module 10. After the pair of extension portions 1034e have been bent upwards (as shown in the dotted lines in FIG. 4C), the vacuum pump module 10 can be installed in the corresponding compartment of the bottom housing module 200 so that the pair of bent extension portions 1034e can secure the flexible intake tube 101 and the exhaust tube 102 winding around the exterior of the soundproofing module 103. In one embodiment of the present invention, the tri-way connector module 40 can be secured to the bottom housing module 200 via a threaded member. In one embodiment of the present invention, the external power source connection port 35 can be defined at an outer side of the bottom housing module 200 while the adaptor 42 that communicates with the air conduit 700 of the oral interface device 70 can be disposed at another outer side opposite thereto. The manner in which the components of the negative pressure generator of the present invention are assembled is shown in FIG. 2. The control module 20 is disposed between the top housing module 300 and the bottom housing module 200 which is shown partially assembled in FIG. 3. In one embodiment of the present invention, the control module 20 is secured over the bottom housing module 200 via a threaded member. The top housing module 300 has a slot 301 defined at a lower portion thereof. A deformable member 30 is disposed in the slot 301, and a cover panel 302 is inlaid above the slot 301 to press against the deformable member 30. The top surface of the cover panel 302 are provided with a plurality of buttons 3020 corresponding to different functions executed through the control module 20. A button 3020 will press against a corresponding portion of the deformable member 30 electrically connected to the control module 20 when being pressed by the user, thereby causing the control module 20 to execute the desired function. In the first embodiment of the present invention, the negative pressure generator further comprises a protective cover 400 covering over the top housing module 300. The protective cover 400 has a cavity 402 defined at a lower portion thereof. The buttons 3020 of the cover panel 302 are exposed after being engaged with the cavity 402 so that the user can press any of them to execute the desired function correspondingly. The front cover module 500 of the negative pressure generator of the present invention is disposed at the front sides of the bottom housing module 200 and the top housing module 300. The front cover module 500 comprises a front cover 502, a sliding bump 504, a position limiting bump 506 and a positioning threaded member 508. The front cover 502 has an accommodation hole 5020, a pair of first engaging members 5022 and a pair of second engaging members 5024. The sliding bump 504 passes through the accommodation hole 5020 and abuts against a slanted surface of the position limiting bump 506. The positioning threaded member 508 is threadedly engaged with the front cover 502 at a proper position and abuts against the position limiting bump 506 to position the sliding bump 504 and the position limiting bump 506. Moreover, the pair of first engaging members 5022 are engaged with a pair of corresponding engaging slots defined on the bottom housing module 200, and the pair of second engaging members 5024 are engaged with a pair of corresponding engaging slots defined on the top housing module 300. The present invention also discloses the assembling of the bottom housing module 200 and the top housing module 300 through threaded engagement by using, for example, various threaded members and the corresponding threaded holes illustrated in FIG. 2.

Figure 9B:
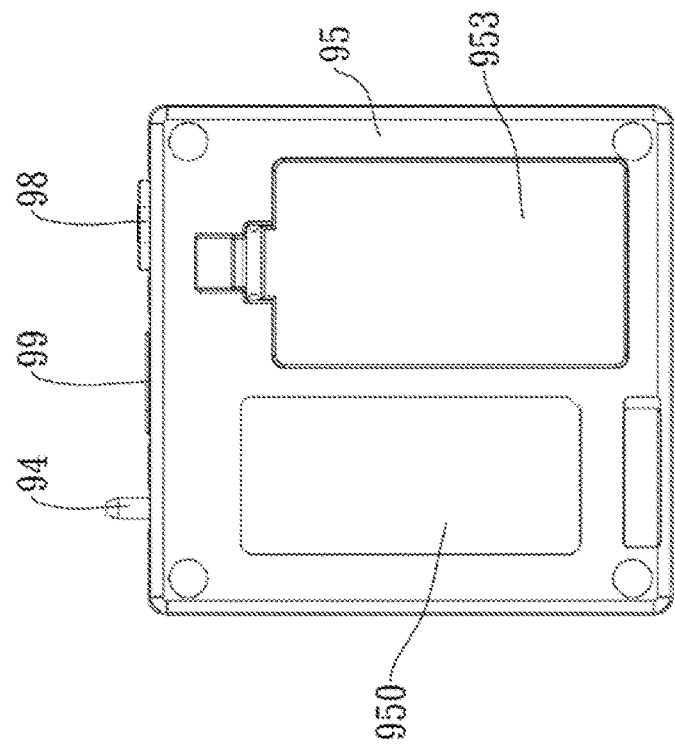
FIG. 9B shows a bottom view of the negative pressure generator according to the second embodiment of the present invention.
Figure 9A:
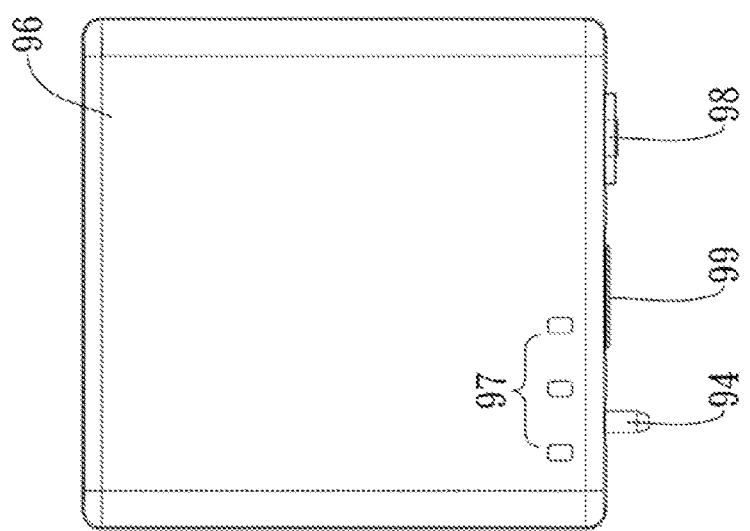
FIG. 9A shows a top view of a negative pressure generator according to the second embodiment of the present invention.
Figure 9D:
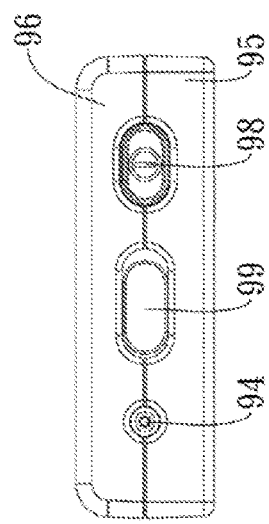
FIG. 9D shows a rear view of the negative pressure generator relative to the bottom view of FIG. 9B according to the second embodiment of the present invention.
Figure 9F:
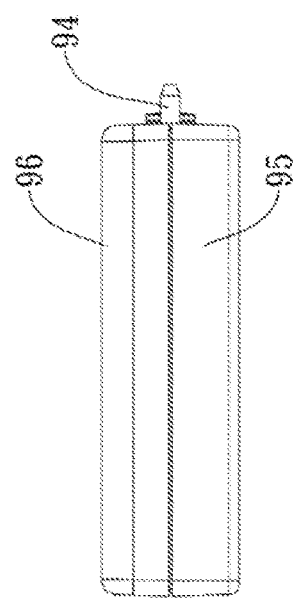
FIG. 9F shows a right side view of the negative pressure generator relative to the bottom view of FIG. 9B according to the second embodiment of the present invention.
Figure 9C:
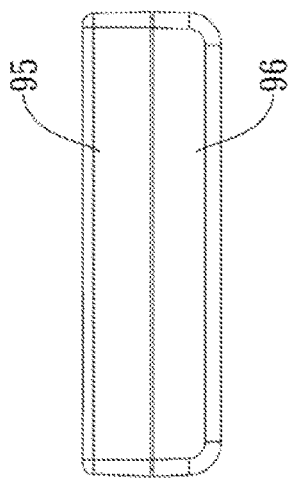
FIG. 9C shows a front view of the negative pressure generator relative to the bottom view of FIG. 9B according to the second embodiment of the present invention.
Figure 9E:
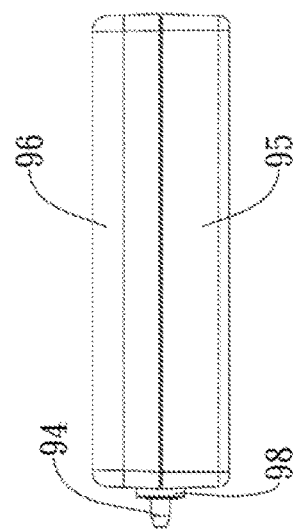
FIG. 9E shows a left side view of the negative pressure generator relative to the bottom view of FIG. 9B according to the second embodiment of the present invention.
Figure 10:
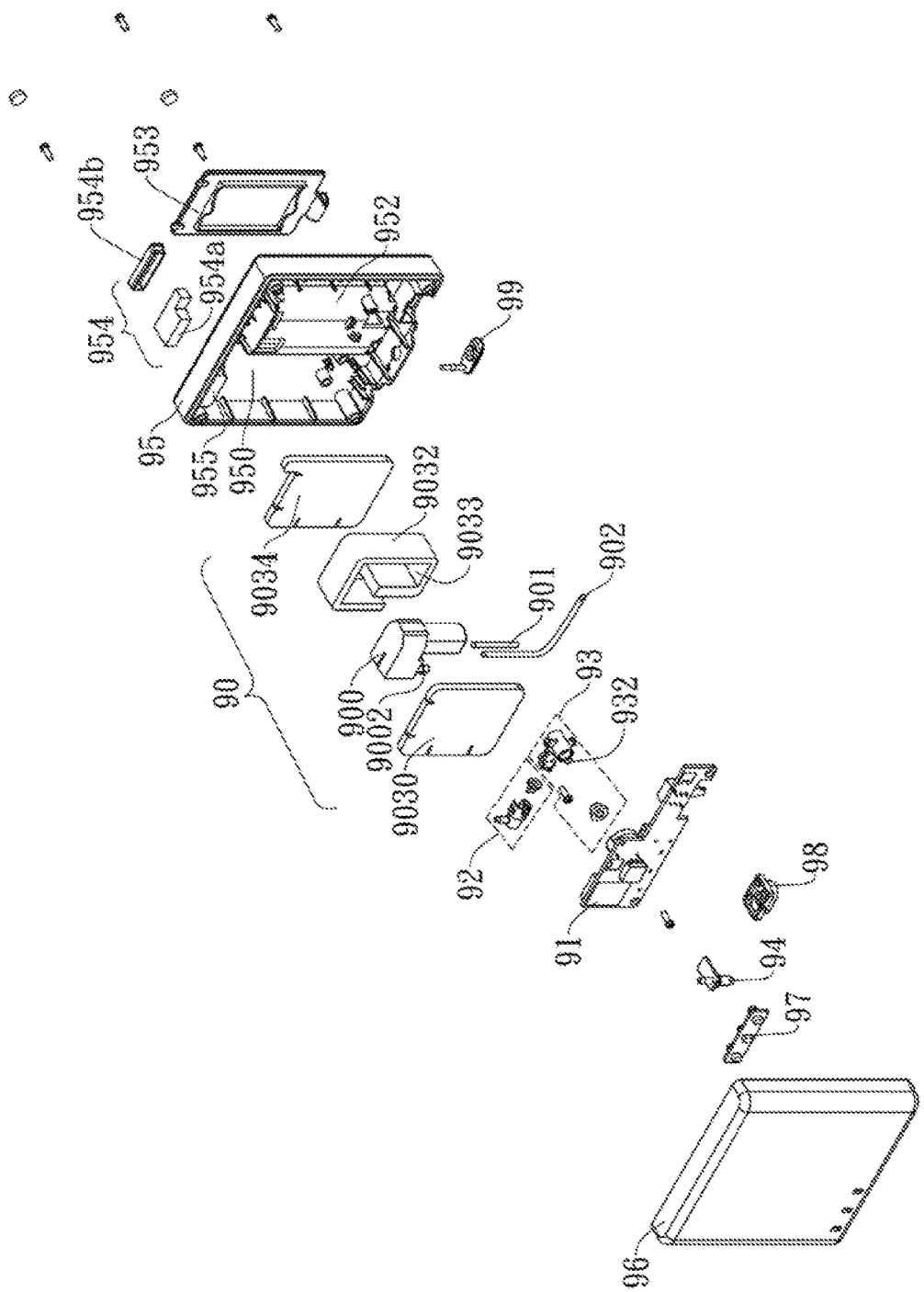
FIG. 10 is a perspective exploded view of the negative pressure generator according to the second embodiment of the present invention.
Figure 11:
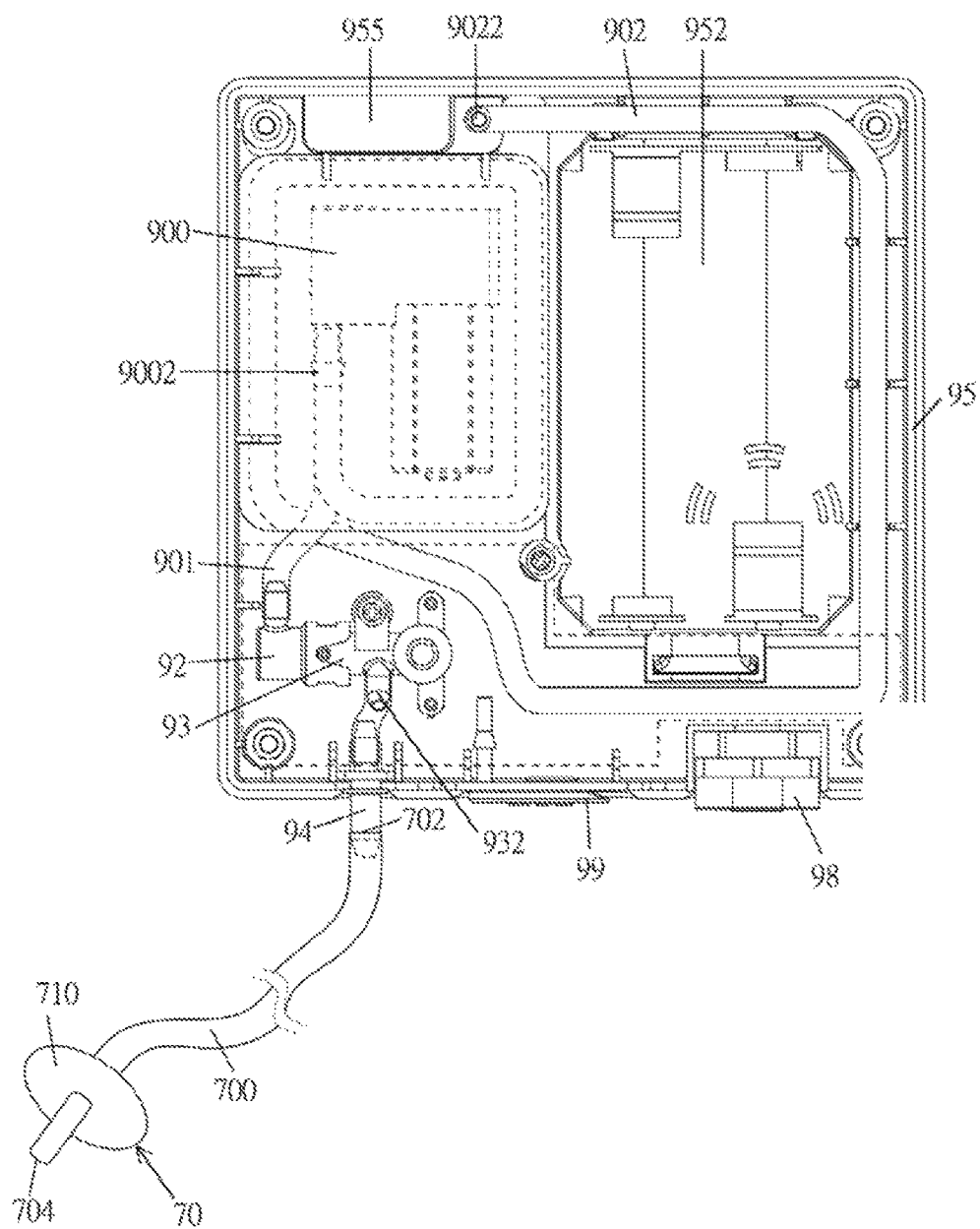
FIG. 11 is a diagram showing an arrangement relationship among the components of a bottom housing module of the negative pressure generator according to the second embodiment of the present invention.

FIG. 9, FIG. 10 and FIG. 11 show a negative pressure generator according to the second embodiment of the present invention. FIG. 9A through FIG. 9F illustrates various aspects of the appearance of the negative pressure generator according to the second embodiment of the present invention, in which FIG. 9A is a top view, FIG. 9B is a bottom view, FIG. 9C is a front view relative to the bottom view of FIG. 9B, FIG. 9D is a rear view relative to the bottom view of FIG. 9B, FIG. 9E is a left side view relative to the bottom view of FIG. 9B, and FIG. 9F is a right side view relative to the bottom view of FIG. 9B. FIG. 10 is a perspective exploded view of the negative pressure generator according to the second embodiment of the present invention. FIG. 11 is a diagram showing an arrangement relationship among the components of a bottom housing module of the negative pressure generator connected with an oral interface device according to the second embodiment of the present invention. In the second embodiment of the present invention, the oral interface device to which the negative pressure generator is applicable is the same as that of the first embodiment. As shown in FIG. 10, the negative pressure generator mainly comprises a vacuum pump module 90, a control module 91, a bottom housing module 95, a top housing module 96 and a power supply source. In the second embodiment, the power supply source is the battery pack (not shown) installed in a battery holder 952 of the bottom housing module 95. A battery holder cover 953 is provided with engaging blocks at two opposing sides thereof to engage with the corresponding engaging recesses of the bottom housing module 95 so as to cover the battery holder 952 and to serve as a base of the battery holder. The user can simply lift the battery holder cover 953 to replace the battery pack. Referring to FIG. 10 and FIG. 11, the vacuum pump module 90 is disposed in a compartment 950 of the bottom housing module 95 besides the battery holder 952. Referring to FIG. 12A through FIG. 12F, the vacuum pump module 90 comprises a vacuum pump 900, a flexible intake tube 901, a flexible exhaust tube 902 and a soundproofing module 903. The vacuum pump 900 has an intake end 9001 communicating with one open end of the flexible intake tube 901 and an exhaust end 9002 communicating with one open end of the flexible exhaust tube 902. The soundproofing module 903 encloses the vacuum pump 900, the flexible intake tube 901 extends from the intake end 9001 to an exterior of the soundproofing module 903, the flexible exhaust tube 902 extends from the exhaust end 9002 and winds around the exterior of the soundproofing module 903 in a multiple loop configuration. The soundproofing module 903 can insulate the ambient environment against noise and vibration generated when the vacuum pump 900 is in operation. The soundproofing module 903 is made of a material selected from the same group of materials for the soundproofing module 103 in the first embodiment. In one embodiment of the present invention, the soundproofing module 903 can comprise a first cover member 9030, an intermediate housing 9032 and a second cover member 9034, wherein the intermediate housing 9032 has a hollow chamber 9033 for accommodating the vacuum pump 900 (see FIG. 12F). As shown in FIG. 12A through FIG. 12E, the flexible exhaust tube 902 winds around the exterior of the soundproofing module 903 in a multiple loop configuration. With such a multiple loop configuration, the length of the flexible exhaust tube 902 can be extended without increasing the size of the vacuum pump module 90, thereby reducing noise generated at the exhaust end 9002 of the vacuum pump 900 when the vacuum pump 900 is in operation. In the second embodiment of the present invention, the flexible intake tube 901 and the flexible exhaust tube 902 are made of any material selected from the same group of materials used in the first embodiment.

Moreover, the variations illustrated in FIG. 5 through FIG. 8 are applicable to the second embodiment as well. An ordinarily skilled person in the art knows how to apply these variations to the negative pressure generator of the second embodiment of the present invention in view of the content disclosed above.

Referring to FIG. 10 and FIG. 11, the negative pressure generator of the second embodiment of the present invention further comprises a check valve module 92, a tri-way connector module 93 and an adaptor 94. The check valve module 92 and the tri-way connector module 93 are disposed at the lower portion of the compartment 950 of the bottom housing module 95. One end of the check valve module 92 communicates with one open end of the flexible intake tube 901 opposite to the open end thereof facing the intake end 9001, and the other end of the check valve module 92 communicates with one port of the tri-way connector module 93. The adaptor 94 communicates with another port 932 of the tri-way connector module 93 and passes through the respective one sides of the top housing module 96 and the bottom housing module 95 (as shown in FIG. 9D). One open end of the air conduit 700 of the oral interface device 70 communicates with the adaptor 94 through which the air conduit 700 communicates with the flexible intake tube 901. When the negative pressure generator of the present invention provides a vacuum source to the oral interface device 70, the air conduit 700, the flexible intake tube 901, the vacuum pump 900 and the flexible exhaust tube 902 constitute a negative pressure path so as to create a negative pressure environment in the user's oral cavity. The check valve module 92 can direct air in the negative pressure path to flow from the air conduit 700 to the flexible exhaust tube 902. An indentation 955 is defined at one top corner of the compartment 950 of the bottom housing module 95 to receive an exhaust filter component 954 comprising a cotton filter pad 954a and an exhaust vent cover 954b. The exhaust vent cover 954b engages with the indentation 955 to secure the cotton filter pad 954a inside the indentation 955. Referring to FIG. 11, one open end 9022 of the flexible exhaust tube 902 opposite to the open end thereof facing the exhaust end 9002 communicates with the cotton filter pad 954a inside the indentation 955 and discharges air sucked by the vacuum pump 900 to the ambient environment via the cotton filter pad 954a and the exhaust vent cover 954b. In one embodiment of the present invention, another port of the tri-way connector module 93 can be connected to a pressure sensor (not shown) disposed in the control module 91 so as to detect a negative pressure value of the negative pressure path. In one embodiment of the present invention, the power supply source is electrically connected to the control module 91 through which the magnitude of the power supplied to the vacuum pump 900 can be controlled so as to favorably reach a desired negative pressure value in the user's oral cavity. In other words, the control module 91 can adjust the magnitude of the power supplied to the vacuum pump 900 according to the negative pressure value detected by the pressure sensor. As shown in FIG. 10 and FIG. 9D, in one embodiment of the present invention, the negative pressure generator further comprises a power switch 98 and a communication connection port 99. The power switch 98 is electrically connected to the control module 91, and the user can press the power switch 98 to turn on or turn off the power supply via the control module 91. The communication connection port 99 is electrically connected to the control module 91, and the user can select the operation mode of the vacuum pump 900 through the communication connection port 99.

In the second embodiment of the present invention, the negative pressure generator can further comprise a warning device 97 electrically connected to the control module 91 and passing through the outer surface of the top housing module 96 so that the state presented on the warning device 97 can be observed easily. The warning device 97 can call the attention of the user or another person near the user to the usage condition of the negative pressure generator. In one embodiment of the present invention, the warning device 97 can be embodied by an LED light set comprising a plurality of LED indicators of different colors. For example, when the pressure sensor detects that the negative pressure value of the negative pressure path has been below a predetermined value, the control module 91 can light up an LED indicator of a certain color to call the attention of the user or another person near the user to the likely occurrence of an air leakage or occlusion of the air conduit of the negative pressure generator. When the negative pressure value of the negative pressure path detected by the pressure sensor is stable, the control module 91 can light up another LED indicator of a different color to indicate that the negative pressure generator functions normally.

The above-mentioned embodiments of the present invention are exemplary and are not intended to limit the scope of the present invention. Various variation or modifications made without departing from the spirit of the present invention and achieving equivalent effects shall fall within the scope of claims of the present invention.

What is claimed is:

1. A negative pressure generator, characterized by comprising:
   a vacuum pump having an intake end and an exhaust end;
   a soundproofing module having a compartment for accommodating the vacuum pump, the soundproofing module being configured to insulate noise and vibration generated when the vacuum pump is in operation; and
   a silencing tube module comprising a flexible intake tube having one open end communicating with the intake end of the vacuum pump and a flexible exhaust tube having one open end communicating with the exhaust end of the vacuum pump, the silencing tube module being configured to reduce noise generated at the intake end and/or the exhaust end of the vacuum pump when the vacuum pump is in operation and disposed on a surface of the soundproofing module; wherein the flexible exhaust tube extends outwards from the exhaust end to wind around an exterior of the soundproofing module in a multiple loop configuration.

2. The negative pressure generator of claim 1, wherein the soundproofing module and the silencing tube module are made of a material selected from a group consisting of silicone, plastic, ethylene vinyl acetate copolymer (EVA) and polyurethane (PU).

3. The negative pressure generator of claim 1, wherein the negative pressure generator is a portable device with a built-in power supply.

4. An apparatus for generating negative pressure in a user's oral cavity, characterized by comprising:
   the negative pressure generator of claim 1; and
   an oral interface device comprising an oral interface and an air conduit having an inlet and an outlet and passing through the oral interface, the oral interface being adapted to be placed in the user's oral cavity to secure the inlet of the air conduit in the user's oral cavity, the outlet of the air conduit communicating with another open end of the flexible intake tube; the air conduit, the flexible intake tube, the vacuum pump and the flexible exhaust tube constitute a negative pressure path so as to create a negative pressure environment in the user's oral cavity.

5. The apparatus for generating negative pressure in a user's oral cavity of claim 4, wherein the soundproofing module and the silencing tube module are made of a material selected from a group consisting of silicone and plastic.

6. A negative pressure generator, characterized by comprising:
   a vacuum pump having an intake end and an exhaust end;
   a soundproofing module comprising a first cover member, an intermediate housing having a compartment for accommodating the vacuum pump and a second cover member, the soundproofing module being configured to insulate noise and vibration generated when the vacuum pump is in operation; and a silencing tube module comprising a flexible intake tube having one open end communicating with the intake end of the vacuum pump and a flexible exhaust tube having one open end communicating with the exhaust end of the vacuum pump, the silencing tube module being configured to reduce noise generated at the intake end and/or the exhaust end of the vacuum pump when the vacuum pump is in operation; wherein the flexible exhaust tube comprises at least one first multiply bent tube disposed inside the first cover member of the soundproofing module, and the flexible exhaust tube comprises a plurality of first multiply bent tubes connected in parallel.

7. The negative pressure generator of claim 6, wherein the flexible intake tube comprises at least one second multiply bent tube disposed inside the second cover member.

8. The negative pressure generator of claim 7, wherein the flexible intake tube comprises a plurality of second multiply bent tubes connected in parallel.

9. A negative pressure generator, characterized by comprising:

a vacuum pump having an intake end and an exhaust end;

a soundproofing module comprising a first cover member, an intermediate housing having a compartment for accommodating the vacuum pump and a second cover member, the soundproofing module being configured to insulate noise and vibration generated when the vacuum pump is in operation; and a silencing tube module comprising a flexible intake tube having one open end communicating with the intake end of the vacuum pump and a flexible exhaust tube having one open end communicating with the exhaust end of the vacuum pump, the silencing tube module being configured to reduce noise generated at the intake end and/or the exhaust end of the vacuum pump when the vacuum pump is in operation; wherein the flexible exhaust tube is arranged in a grating-shaped loop configuration on a surface of the first cover member opposite to a surface thereof facing the vacuum pump, and a porous material is filled in the flexible exhaust tube.

10. The negative pressure generator of claim 9, wherein the flexible intake tube is arranged in a grating-shaped loop configuration on a surface of the second cover member opposite to a surface thereof facing the vacuum pump, and a porous material is filled in the flexible intake tube.

* * * * *